United States Patent [19]

van der Meer et al.

[11] Patent Number: 4,668,257
[45] Date of Patent: May 26, 1987

[54] WATER SEPARATOR FOR A GAS ANALYZER

[75] Inventors: Jelle van der Meer, Amerongen; Hans Slaghuis, Arnhem, both of Netherlands

[73] Assignee: Gould Electronics B.V., Netherlands

[21] Appl. No.: 737,389

[22] Filed: May 23, 1985

[30] Foreign Application Priority Data

May 30, 1984 [NL] Netherlands ................. 8401757

[51] Int. Cl.$^4$ ............................................. B01D 45/08
[52] U.S. Cl. ......................................... 55/267; 55/462
[58] Field of Search ................. 55/267–269, 55/391, 434, 319, 462–465, DIG. 17

[56] References Cited

U.S. PATENT DOCUMENTS

| | | | |
|---|---|---|---|
| 1,391,989 | 9/1921 | Zoppel | 55/464 |
| 1,442,689 | 1/1923 | Loss | 55/463 |
| 2,720,278 | 10/1955 | Wiley | 55/DIG. 17 |
| 4,197,858 | 4/1980 | Osborn . | |

FOREIGN PATENT DOCUMENTS

| | | | |
|---|---|---|---|
| 71064 | 1/1916 | Austria | 55/391 |
| 1648925 | 10/1972 | Fed. Rep. of Germany . | |
| 505729 | 4/1920 | France . | |
| 623717 | 6/1927 | France . | |
| 876738 | 9/1961 | United Kingdom . | |
| 2029959 | 3/1980 | United Kingdom . | |

*Primary Examiner*—Bernard Nozick
*Attorney, Agent, or Firm*—Pahl, Lorusso & Loud

[57] ABSTRACT

The invention relates to a water separator for a gas analyzer with a water separation chamber formed in a housing, a supply and a discharge for the gas to be analyzed being connected with said chamber and a collection reservoir for the separated water being positioned below said water separation chamber. The water separation chamber consists of a conical and annular space having a diameter that decreases towards the collection reservoir and wherein the supply and the discharge debouch in that part of the annular space having substantially the greatest diameter. This results in a very effective separation of the water and the gas. A water lock can be provided between the annular space and the collection reservoir, said water lock limiting the dead space. The water separator can further be improved by cooling at least one wall of the annular space.

10 Claims, 1 Drawing Figure

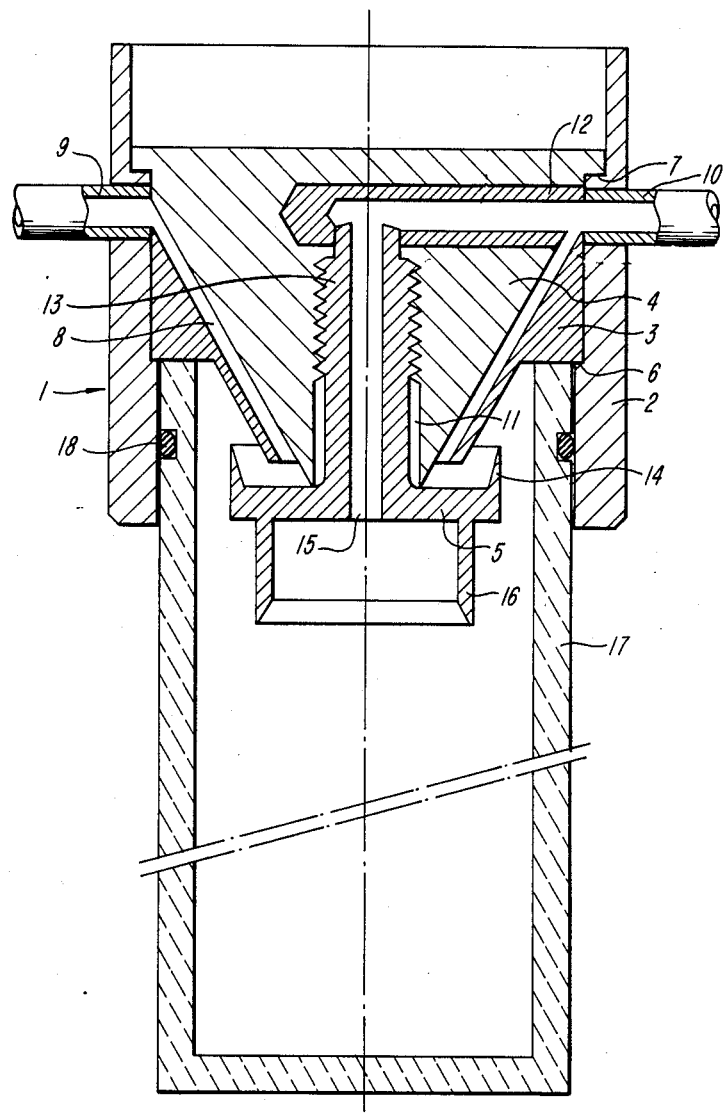

WATER SEPARATOR FOR A GAS ANALYZER

The invention relates to a water separator for a gas analyser with a water separation chamber formed in a housing, a supply and a discharge for the gas to be analysed being connected with said chamber and a collection reservoir for the separated water being positioned below said water separation chamber.

In the medical field gas analysers are often used, for example for measuring the percentage of carbondioxide in the expirated air of a patient during an operation. Because the temperature of the expirated air is considerably higher than the temperature in the conduits of the gas analyser the water vapour in the gas sample will condensate and appear as small drops in these conduits. For the accuracy of the measurement it is essential that these water vapour drops will not enter the measurement region of the gas analyser itself, because this would cause a temporal disturbance of the measurement.

A known gas analyser comprises a water separation chamber from which the separated water is led to a collection reservoir for the water. The water separation chamber has a downwardly tapering form for collecting the separated water.

It is an object of the invention to provide a water separator that separates water from the gas to be analysed in a very simple but nevertheless very effective way without essentially disturbing the current composition of the gas to be analysed excepted for the water vapour concentration.

To this end the water separator according to the invention is characterized in that the water separation chamber consists of a conical and annular space having a diameter that decreases towards the collection reservoir and wherein the supply and the discharge debouch in that part of the annular space having substantially the greatest diameter.

The conical and annular space with a diameter that decreases towards the collection reservoir provides a very effective separation of the water and gas. Forced by the gravity the water will move downwardly along the wall of the annular space. The gas debouching into the annular space at its widest diameter through the supply will move through the annular space essentially in the same horizontal plane along two semi circular paths and reach the discharge. The downwardly decreasing diameter of the annular space prevents a downward flow of the gas because this would incorporate a sharper curvature of the followed path which energetically (it would cost more energy) cannot or can hardly be carried out by the gas.

In a preferred embodiment of the water separator according to the invention this is characterized by a water lock between the annular space and the collection reservoir. This water lock between the annular space and the collection reservoir at one side allows the collection of water in the collection reservoir but at the other side forms an effective barrier for the gas to be analysed. This considerably limits the volume of the dead space in a very simple but effective way, the more because the volume of the water separation chamber is already extremely small because of the special shape of the annular space. The importance of a small volume of the space formed by the water separation chamber and the collection reservoir lies in the fact that a small volume leads to a short reaction time of the measurement so that the gas analyser can follow quickly the variations in the composition of the gas to be analysed, for example expirated air during different phases of the expiration cycle.

In a further preferred embodiment of the water separator according to the invention the collection reservoir is connected with the discharge by means of an air breather. This air breather that is connected with the discharge controls the discharge of air from the collection reservoir. Because this air breather is connected with the discharge the air is directly sucked away from the discharge without the need for special arrangements.

According to a still further adventageously usable embodiment at least one wall of the annular space is cooled, so that the water separation power will be increased still further. As a result of this cooling apart from the water already present as drops also the water vapour present in the gas will be condensated and separated.

In a preferred embodiment of the water separator according to the invention the conical and annular space is formed by a funnel shaped, at its lower side open first body positioned in the housing and a conical second body positioned therein at a small distance therefrom.

In this way in a constructively easy way an annular space is created the geometry of which can be varied if so desired or needed by using different bodies.

Further it is preferred that the lower part of the second body extends slightly below the first body and the water lock is formed by an element secured to the lower side of the second body and having an upstanding edge that extends above the lower end of the first body.

The connection to the lower part of the second body of an element functioning as a water lock and having an upstanding edge that extends above the lower end of the first body provides for a small water reservoir at that place, the water level of which defined by the upstanding edge reaches into the annular space. Due to the capillary action of the annular space the water will partially fill up the annular space thereby still further reducing the dead space.

The invention will hereafter be explained further with reference to the drawing in which a vertical section of an embodiment is shown.

The water separator 1 mainly consists of a housing 2, a funnel shaped first body 3, a conical shaped second body 4 and an element 5 functioning as a water lock. The housing 2 is formed in such a way that the bodies 3, 4 maintain therein a certain relative position. To this end the first body 3 rests on a first round going supporting edge 6, while the second body 4 rests on a second round going supporting edge 7.

The first and second bodies 3, 4 form a conical and annular space 8 the diameter of which decreases downwardly. Into the upper section of the annular space 8 a supply 9 and a discharge 10 debouch. As appears clearly from the drawing this supply 9 and discharge 10 are placed in the housing 2 opposite of each other for a good functioning of the water separator 1.

The second body 4 can be manufactured of a good heat conducting material, such as aluminium and can be cooled. For the cooling each known method can be used, such as placing a cooling element on top of the second body 4. At the lower side of the second body 4 the element 5 is secured that is mountable, for example screwable, in a channel 11 in the second body 4. This channel extends into the upper part of the annular space 8 and consists of two sections, one of which extends vertically and the other horizontally. The horizontal channel section is covered with a heat insulating material 12 ensuring an insulation of the air that is led through the channel 11 relative to the cooled second body 4. The vertical section of the channel 11 is also heat-insulated by the screwed in shaft 13 of element 5. The upper end of this shaft 13 fits closely to the heat-insulating material 12 of the horizontal channel section. The location of the channel 11 in the second body 4 is such that this channel 11 debouches in the annular space 8 near the discharge 10.

The element 5 acting as a water lock has an upstanding edge 14 that extends above the lower end of the first body 3. As a result the water level in the element 5 will reach into the annular space 8 in which the water will rise due to capillary action. The element 5 is provided with a central bore 15 that extends along the total length of the element 5. Furthermore the element 5 is at its lower side provided with a downwardly projecting annular edge 16 with a small wall thickness. This edge 16 is bevelled at its end and enables a correct drop forming of the water while moreover it will be prevented that the central bore 15 will be sealed by water drops or a water film.

The housing 2 contains a collection reservoir 17 that is releaseably secured to the housing 2 by means of a sealing and clamping ring 18.

The gas that is led into the annular space 8 through the supply 9 will flow towards the discharge 10 by semi circular paths that are positioned perpendicularly to the plane of the drawing. Hereby this gas contacts the cooled second body 4 so that the water vapour in the gas will condensate and move downwardly through the annular space 8 towards element 5. As a result a part of the water already present in element 5 will flow over the upstanding edge 14 of the element 5 and drip in the collection reservoir 17 via the downwardly projecting edge 16. The pressure in the collection reservoir 17 is maintained on a constant level by the air breather that is formed by the central bore 15 in the shaft 13 of the element 5 and the horizontal section of the channel 11 in the second body 4, so that the flow of the water through the element 5 will not be impeded. When water is led in the collection reservoir 17 the air breather provides the discharge of a corresponding volume of air from the collection reservoir 17, also as a result of the lower pressure that results in the air breather due to the action of the discharge 10, close to which the air breather debouches.

When the collection reservoir 17 is filled up this can easily be replaced by a new empty reservoir.

The invention is not limited to the embodiment described above but can be varied widely within the scope of the invention. Thus it is possible to apply the invention on other fields than the medical field. Hereby can be thought of industrial applications.

We claim:

1. A water separator for separating water from a gas to be analyzed by a gas analyzer comprising:
   a water separation chamber which is supported by a housing wherein the water separation chamber comprises a funnel shaped first body open at its lower side and a conical shaped second body, wherein the first body is fixedly positioned relative to the second body so that the first body and the second body form a conical and annular space therebetween having a diameter that decreases downwardly and wherein the water separated from the gas to be analyzed passes downwardly through the conical and annular space by force of gravity;
   a supply for introducing the gas to be analyzed into the water separation chamber which is receivable through an opening in the housing having a first end for receiving the gas and a second end which is connected to the water separation chamber wherein the second end communicates with the conical and annular space at its greatest diameter;
   a discharge for removing the gas to be analyzed from the water separation chamber which is receivable through an opening in the housing having a first end connected to the water separation chamber at a location diametrically opposite the connection of the supply to the water separation chamber and a second end for discharging the gas to be analyzed, wherein the first end communicates with the conical and annular space at that part of the conical and annular space having the greatest diameter which is diametrically opposite the position where the second end of the supply communicates with the conical and annular space, such that the flow of the gas to be analyzed through the separation chamber, from the supply to the discharge, is in a semi-circular path along the horizontal plane defined by the supply and discharge; and
   a collection reservoir securable to the housing, for collecting the water separated from the gas after it passes downwardly through the conical and annular space.

2. The water separator according to claim 1, wherein the second body is manufactured of aluminum.

3. The water separator according to claim 1 wherein the lower part of the second body extends slightly below the first body.

4. A water separator for separating water from a gas to be analyzed by a gas analyzer comprising:
   a water separation chamber which is supported by a housing wherein the water separation chamber comprises a first body and a second body wherein the first body is fixedly positioned relative to the second body so that the first body and the second body form a conical and annular space therebetween having a diameter that decreases downwardly and wherein the water separated from the gas to be analyzed passes downwardly through the conical and annular space by force of gravity;
   a supply for introducing the gas to be analyzed into the water separation chamber which is receivable through an opening in the housing having a first end for receiving the gas and a second end which is connected to the water separation chamber wherein the second end communicates with the conical and annular space at its greatest diameter;
   a discharge for removing the gas to be analyzed from the water separation chamber which is receivable through an opening in the housing having a first end connected to the water separation chamber at a location diametrically opposite the connection of the supply to the water separation chamber and a second end for discharging the gas to be analyzed, wherein the first end communicates with the conical and annular space at that part of the conical and annular space having the greatest diameter which is diametrically opposite the position where the second end of the supply communicates with the conical and annular space;

a collection reservoir securable to the housing, for collecting the water separated from the gas; and means for receiving water which is secured to the lower side of the second body and which is disposed relative to the collection reservoir so that water overflow from the means for receiving water falls into the collection reservoir, wherein when filled with water, the water level of the means for receiving water reaches into the conical and annular space due to the capillary action existing therein, whereby the downward movement of the water separated from the gas to be analyzed through the conical and annular space against the water level of the means for receiving water which reaches into the conical and annular space forces some water in the means for receiving water to drip into the collection reservoir.

5. The water separator according to claim 4 wherein the means for receiving water includes a water lock having a bottom and an upstanding peripheral edge that extends above the lower end of the first body.

6. The water separator according to claim 5, wherein the water lock further comprises an annular edge having a small wall thickness which projects downwardly from the water lock bottom.

7. The water separator according to claim 6, wherein the annular edge is bevelled downwardly.

8. The water separator according to claim 5 wherein the water lock further comprises a central shaft extending vertically from the bottom which is mounted within a vertical channel in the second body wherein the central shaft has a bore that extends through its total length which communicates at one end with the collection reservoir and at the other end with a horizontal channel in the second body, wherein the horizontal channel is closed at one end and at the other end communicates with the discharge and the conical and annular space.

9. The water separator according to claim 8, wherein the horizontal channel in the second body is insulated.

10. The water separator according to claim 8, wherein the water lock is formed of heat-insulating material which insulates the central bore of the water lock.

* * * * *